(12) United States Patent
Golz et al.

(10) Patent No.: US 7,879,557 B2
(45) Date of Patent: Feb. 1, 2011

(54) **ISOLATED FLUORESCENT PROTEIN FROM *CLYTIA GREGARIA* CGFP AND USE THEREOF**

(75) Inventors: Stefan Golz, Essen (DE); Svetlana Markova, Krasnoyarsk (RU); Ludmila Burakova, Sosnovoborsk (RU); Ludmila Frank, Krasnoyarsk (RU); Eugene Vysotski, Krasnoyarsk (RU)

(73) Assignee: Bayer Schering Pharma Aktiengsellschaft, Berlin (DE)

( * ) Notice: Subject to any disclaimer, the term of this patent is extended or adjusted under 35 U.S.C. 154(b) by 0 days.

(21) Appl. No.: 10/537,614

(22) PCT Filed: Nov. 26, 2003

(86) PCT No.: PCT/EP03/13281

§ 371 (c)(1),
(2), (4) Date: Feb. 6, 2006

(87) PCT Pub. No.: WO2004/052926

PCT Pub. Date: Jun. 24, 2004

(65) Prior Publication Data

US 2006/0188930 A1    Aug. 24, 2006

(30) Foreign Application Priority Data

Dec. 9, 2002   (DE) .............................. 102 57 354

(51) Int. Cl.
  *G01N 33/53*   (2006.01)
  *C07H 21/04*   (2006.01)
  *C12P 21/06*   (2006.01)
  *C07K 14/435*  (2006.01)

(52) U.S. Cl. .................. 435/7.1; 435/69.1; 435/320.1; 435/252.3; 435/325; 530/350; 536/23.5

(58) Field of Classification Search .................. None
See application file for complete search history.

(56) References Cited

U.S. PATENT DOCUMENTS 5,777,079 A * 7/1998 Tsien et al. ................. 530/350
6,096,865 A * 8/2000 Michaels ..................... 530/350

OTHER PUBLICATIONS

Levine et al (Compar. Biochem. Physiol. B, 1982. 72;1:77-86).*
Fraile-Ramos et al. (Molecular Biology of the Cell. Jun. 2001; 12: 1737-1749).*
Roger Tsien. (Annu. Rev Biochem. 1998. 67: 509-544).*
TC1600 memo.*
Levine, et al., "Isolation and Characterization of a Photoprotein 'Phialidin' and a Spectrally Unique Green-Fluorescent Protein from the Bioluminescent Jellyfish *Phialidium gregarium*," *Comp. Biochem. Physiol.*, 72B: 77-85 (1982).
Chalfie, et al., "Green Fluorescent Protein: Properties, Applications, and Protocols," Aug. 1998, Wiley-Liss, Inc., pp. 49 and 70.
Prasher, D.C., "Using GFP to See the Light," *Trends in Genetics*, 11 (8): 320-323 (1995).
Tsien, R.Y., "The Green Fluorescent Protein," *Annu. Rev. Biochem.*, 67: 509-544 (1998).
Inouye, et al., "Cloning and Sequence Analysis of cDNA for the Ca2+-activated Photoprotein, Clytin," *FEBS*, 315 (3):343-346 (1993).
Prasher, et al., "Primary Structure of the *Aequorea victoria* Green-Fluorescent Protein," *Gene*, 111: 229-233 (19920.
[Database GenBank Online] Prasher, et al., "Primary Structure of the *Aequorea victoria* Green-Fluorescent Protein," Database Accession No. M62653.

* cited by examiner

*Primary Examiner*—Scott Long
(74) *Attorney, Agent, or Firm*—Thomas C. Blakinship; Edwards Angell Palmer & Dodge LLP; Gabriel J. McCool

(57) ABSTRACT

The invention relates to the nucleotide and amino acid sequences and to the activity and use of the fluorescent protein CGFP.

10 Claims, 11 Drawing Sheets

```
CGFP_Cly 000:MTALTEGAKLFEKEIPYITELEGDVEGMKFIIKGEGTGDATTGTIKAKYICTTGD-LPVP
GFP_Aeq  000:....MSKGEELFTGVVPILVELDGDVNGQKFSVSGEGEGDATYGKLTLKFICTTGK-LPVP
GFP_Ren  000:MSKQILKNTCLQEVMSYKVNLEGIVNNHVFTMEGCGKGNILFGNQLVQIRVTKGAPLPFA

CGFP_Cly 060:WATILSSLSYGVFCFAKYPRHIA--DFFKSTQPDGYSQDRIISFDNDGQYDVKAKVTYEN
GFP_Aeq  060:WPTLVTTFSYGVQCFSRYPDHMKQHDFFKSAMPEGYVQERTIFYKDDGNYKTRAEVKFEG
GFP_Ren  060:FDIVSPAFQYGNRTFTKYPNDIS--DYFIQSFPAGFMYERTLRYEDGGLVEIRSDINLIE

CGFP_Cly 120:GTLYNRVTVKGTGFKSNGNILGMRVLYHSPPHAVYILPDRKNGGMKIEYNKAFDVMGGGH
GFP_Aeq  120:DTLVNRIELKGIDFKEDGNILGHKMEYNYNSHNVYIMADKPKNGIKVNFKIRHNIKDGSV
GFP_Ren  120:DKFVYRVEYKGSNFPDDGPVMQKTILGIEPSFEAMYM----NNGVLVGEVILVYKLNSGK

CGFP_Cly 180:QMARHAQFNKPLGAWEEDYPLYHHLT--VWTSFGKDPDDDETDHLTIVEVIKAVDL----
GFP_Aeq  180:QLADHYQQNTPIGDGPVLLPDNHYLS--TQSALSKDP-NEKRDHMILLEFVTAAGITHGM
GFP_Ren  180:YYSCHMKTLMKSKGVVKEFPSYHFIQHRLEKTYVEDGGFVEQHETAIAQMTSIGKPLGSL

CGFP_Cly 240:-ETYR
GFP_Aeq  240:DELYK
GFP_Ren  240:HEWV
```

Fig. 7A

```
CGFP_Cly_000:atgactgcacttaccgaaggagcaaaactgttcgagaagaaattccctacattacagag
GFP_Ren _000:atgagtaaaacaaatattgaagaacacttgttacaagaagtaatgtcgtataagtaaat
GFP_Aeq _000:atgagtaaaggagaagaacttttcactggagttgtcccaattcttgttgaattagatggc CGFP_Cly_060:ttggaaggagagcgttgaaggaatgaaattcatcatcaaaggtgaaggtactggcgacgct
GFP_Ren _060:ctgaaggaattgtaaacaaccatgttttttacaatggaggttgcggcaaaggaatatt
GFP_Aeq _060:gatgttaatgggcacaaattctctgtcagtggagaggtgaaggtgatgcaacatacgga CGFP_Cly_120:actactggcaccatcaaagcgaaatatatttgcacaactggtgaccttcctgtaccatgg
GFP_Ren _120:ttattcgcaatcaactggttcagattcgtgtcacgaaagggcccactgccttttgca
GFP_Aeq _120:aaacttaccccttaaaatttattgcactactgggaagctacctgttccatggccaacactt CGFP_Cly_180:gctaccatcttgagtagtttgtcgtatggtgtgttttctgtttcgctaagtatccacgccac
GFP_Ren _180:tttgatattgtgtcaccagctttcaatatggcaaccgtactttcacgaaatatccgaat
GFP_Aeq _180:gtcactactttctcttatggtgttcaatgctttcaagatacccagatcatatgaaacag
```

Fig. 7B

```
CGFP_Cly_240:attgccgacttttcaagagcacacaaccagatggttattcacaagacagaatcattagt
GFP_Ren _240:gatatatcagattattttatacaatcattccagcaggattatgtatgaacgaacatta
GFP_Aeq _240:catgactttttcaagagtgccatgcccgaaggttatgtacaggaaagaactatatttac CGFP_Cly_300:tttgacaatgatggcaatacgatggacaaagccaaggttacttatgaaacggaacactt
GFP_Ren _300:cgttacgaagatggcggactigttgaaattcgttcagatatataaattaatagaagacaag
GFP_Aeq _300:aaagatgacgggaactacaagacacgtgctgaagtcaagtttgaaggtgatacccttgtt CGFP_Cly_360:tataatagagtcacagtcactggcttcaaatcaaacggcaacatccttggtatg
GFP_Ren _360:ttcgtctacagagtgaatacaaggtagtaacttcccagatggtcccgtcatgcag
GFP_Aeq _360:aatagaatcgagtgaaaagtattgatttaaagaagatgaaacattcttggacacaaa CGFP_Cly_000:atgactgcacttaccgaaggagcaaaactgttcgagaaagaaattccctacattacagag
GFP_Ren _000:atgagtaaacaaatattgaagaacacttgtttacaagaagtaatgtcgtataaagtaaat
GFP_Aeq _000:atgagtaaaggagaagaacttttcactggagttgtcccaattcttgttgaattagatggc CGFP_Cly_060:ttggaaggagacgtttgaaggaatgaagttactggcgacgct
GFP_Ren _060:ctggaaggaattgtaaacaaccatgtttttacaatggagggttgcggcaagggaatatt
GFP_Aeq _060:gatgttaatggcaaaaattctctgtcagtggagagggtgaaggtgatgcaacatacgga
```

Fig. 7C

```
CGFP_Cly_120:actactggcaccatcaaagcgaaatatattgcacaactggtgacttcctgtaccatgg
GFP_Ren _120:ttattcggcaatcaactggttcagattcgtgtcacgaaagggccccactgcctttgca
GFP_Aeq _120:aaacttacccttaaatttattgcactactgggaagctacctgttccatggccaacactt CGFP_Cly_180:gctaccatcttgagtagttgtcgtatggtgtgttttctgtttcgctaagtatccacgccac
GFP_Ren _180:tttgatatgtgtcaccagctttcaatatggcaaccgtactttcacgaaatatccgaat
GFP_Aeq _180:gtcactactttctcttatgtgttcaatgctttcaagataccagatcatatgaaacag CGFP_Cly_240:attgccgactttccaagagcacacaaccagatggttattcacagacagaatcattagt
GFP_Ren _240:gatatatcagattatttatacaatcattccaggattatgtgtacggaaaattaatagaagacaag
GFP_Aeq _240:catgacttttcaagagtgccatgcccgaaggttatgtacaggaagttatgtacaggaagaactatatttac CGFP_Cly_300:tttgacaatgatgacaatacgatgtcaaagccaaggttacttatgaaaacggaacactt
GFP_Ren _300:cgttacgaagatggcggacttgttgaaattcgttcagatataaattaatagaagacaag
GFP_Aeq _300:aaagatgacgggaactacaagacacgtgctgaagtcaagtttgaaggtgatacccttgtt CGFP_Cly_360:tataatagagtcacagagtcaaaggtactggcttcaaatcaaacggcaacatccttggtatg
GFP_Ren _360:ttcgtctcacagagtggaatacaaaggtagtaacttcccagatgatgtcccgtcatgcag
GFP_Aeq _360:aatagaatcgagttaaaaggtattgattttaaagaagatggaaacattcttggacacaaa
```

Fig. 7D

```
CGFP_Cly_420:agagttctctaccattcaccaccacgctgtctacatcctcctgaccgtaaaatggt
GFP_Ren_420:aagactatcttaggaatagagccttcattgaagccatgtacatgaataatggcgtcttg
GFP_Aeq_420:atggaatacaactataactcacataatgtatacatcatggcagacaaaccaaagaatgga CGFP_Cly_480:ggcatgaaaattgaatacaataaggctttcgacgttatgggcggtggtcaccaaatggcg
GFP_Ren_480:gtcggcgaagtaattctgtctataaactaaactctggaaatattattcatgtcacatg
GFP_Aeq_480:atcaaagttaacttcaaaattagacacacattaaagatggaagcgttcaattagcagac CGFP_Cly_540:cgtcacgcccaattcaataaaccactaggagcctgggaagaagattatccgttgtatcat
GFP_Ren_540:aaaaacattaatgaagtcgaaaggtgtagtaaaggagtttccttcgtatcatttattcaa
GFP_Aeq_540:cattatcaacaaaatactccaattggcgatggccctgtccttttaccagacaaccattac CGFP_Cly_600:catcttaccgtatggacttctttcggaaaagatccgatgatgatgaaactgaccatttg
GFP_Ren_600:catcgtttggaaagacttacgtagaagactcggggggttcgttgaacagcatgagactgct
GFP_Aeq_600:ctgtccacacaatctgccctttccaaagatcccaacgaaagagagatcacatgatcctt CGFP_Cly_660:accatcgtcgaagtcatcaaagctgttgatttggaaacatacgttga---------
GFP_Ren_660:attgctcaaatgacatctataggaaaaccactaggatccttacacg-------aatg
GFP_Aeq_660:cttgagtttgtaacagctgctgggattacacatggcatgaactatacaaataaatg
```

Fig. 7E

```
CGFP_Cly_720:----------------------
GFP_Ren _720:------g--gt----ttaa
GFP_Aeq _720:tccagacttccaattga
```

ISOLATED FLUORESCENT PROTEIN FROM *CLYTIA GREGARIA* CGFP AND USE THEREOF

The invention relates to the nucleotide and amino acid sequences and to the activity and use of the fluorescent protein CGFP (fluorescence protein of *Clytia gregaria*).

Fluorescent Proteins

A multiplicity of coelenterates are bioluminescent (Morin et al., 1974) and emit blue or green light. *Aequoria victoria* aequorin which was identified as the first light-producing protein in 1962 (Shimomura et al., 1962) emitted, as an isolated protein, a blue light, rather than the phenotypically observed green light of *Aequoria victoria*. Later, the green fluorescent protein (GFP) was isolated from *Aequoria victoria*, which, owing to the excitation by aequorin, makes the medusa appear green phenotypically (Johnson et al, 1962; Hastings et al., 1969; Inouye et al, 1994).

Green fluorescent proteins have been isolated from different organisms. These include the Hydozoa (*aequoria, halistaura obelia*) and anthropods (*acanthotilum*, sea cactus, *cavernularia, renila, ptilosarcus, stylatula*) (Morin et al., 1971; Morin et al., 1971 II, Wampler et-al., 1971, Wampler et al., 1973, Cormier et al., 1973, Cormier et al., 1974, Levine et al., 1982).

A compilation of some fluorescent proteins can be found in Table 1:

TABLE 1

Overview over some fluorescent proteins. Indicated are the name, the organism from which the protein has been isolated and the identification number (Acc. No.) of the database entry.

| Name | Organism | Identification no. |
| --- | --- | --- |
| Green fluorescent protein | *Aequorea macrodactyla* | AF435433 |
| Green fluorescent protein | *Aequoria* | L29345 |
| Green fluorescent protein-like protein | *Agaricia agaricites* | AY037775 |
| Green fluorescent protein-like protein | *Agaricia fragilis* | AY037765 |
| Green fluorescent protein | *Dendronephthya* | AF420591 |
| Red fluorescent protein | *Entacmaea quadricolor* | AY130757 |
| Green fluorescent protein-like protein | Caribbean anemone | AY037777 |
| Green fluorescent protein | *Heteractis crispa* | AF420592 |
| Green fluorescent protein-like protein | *Montastraea annularis* | AY037766 |
| Green fluorescent protein-like protein | *Montastraea cavernosa* | AY037768 |
| Cyan fluorescent protein | *Montastraea cavernosa* | AY056460 |
| Green fluorescent protein | *Renilla muelleri* | AY015996 |
| Green fluorescent protein | *Renilla renoformis* | AF372525 |
| Green fluorescent protein-like protein | *Ricordea florida* | AY037774 |

The fluorescent proteins differ not only due to their nucleotide and amino acid sequences but also due to their biochemical and physical properties. The spectral characteristics of the fluorescent proteins may differ both on the side of excitation and on, the side of emission. An overview of the fluorescence spectra and the excitation wavelength can be found in Table 2.

TABLE 2

Overview over some fluorescent proteins. Indicated are the organism from which the protein has been isolated, the excitation wavelength and emission wavelength determined in spectral analyses.

| Organism | Excitation | Fluorescence |
| --- | --- | --- |
| *Aequoria* | 465-498 nm | 509 nm |
| *Halistaura* | 465 nm | 497 nm |
| *Phialidium* | 485 nm | 498 nm |
| *Renilla* | 498 nm | 508 nm |

The use of fluorescent proteins has already been described previously. An overview can be found in Table 3:

TABLE 3

Overview over some fluorescent proteins. Indicated are the organism from which the protein has been isolated, the name of the fluorescent protein and a selection of patents or applications.

| Organism | Fluorescent protein | Patent/application |
| --- | --- | --- |
| *Renilla mulleri* | GFP | U.S. Pat. No. 6,436,682 |
| | | WO200168824 |
| | | WO200257451 |
| | | WO200134824 |
| | | WO9949019 |
| | | U.S. Pat. No. 6,232,107 |
| *Aequoria* | GFP | WO200071565 |
| | | WO9711094 |
| | | WO9623898 |
| | | U.S. Pat. No. 5,958,713 |
| | | U.S. Pat. No. 6,172,188 |

It was shown that it is possible to alter the physical and biochemical properties of fluorescent proteins by altering the amino acid sequence thereof. Examples of mutagenized fluorescent proteins have been described in the literature (Delagrave et al., 1995; Ehrig et al., 1995; Heim et al., 1996).

Fluorescent proteins are already used in a wide variety of areas. The use of fluorescent proteins in 'Fluorescence Resonance Energy Transfer' (FRET), 'Bioluminescence Resonance Energy Transfer (BRET) and other energy transfer methods has already been described in the literature (Mitra et al., 1996; Ward et al., 1978; Cardullo et al, 1988; U.S. Pat. Nos. 4,777,128; 5,126,508; 4,927,923; 5,279,943). Further nonradioactive methods of energy transfer by means of GFP have likewise been described previously (PCT appl. WO 98/02571 and WO 97/28261)

Reporter Systems

Reporter gene or indicator gene generally refers to genes whose gene products can be readily detected with the aid of simple biochemical or histochemical methods. At least 2 types of reporter genes are distinguished.

1. Resistance genes. Resistance genes refer to genes whose expression imparts to a cell the resistance to antibiotics or other substances whose presence in the growth medium leads to cell death when the resistance gene is absent.
2. Reporter gene. The products of reporter genes are used as fused or nonfused indicators in genetic engineering. The most commonly used reporter genes include beta-galactosidase (Alam et al., 1990), alkaline phosphatase (Yang et al., 1997; Cullen et al., 1992), luciferases and other photoproteins (Shinomura, 1985; Phillips G N, 1997; Snowdowne et al., 1984).

Luminescence refers to the emission of photons in the visible spectral range, said emission being effected by excited emitter molecules. In contrast to fluorescence, the energy is supplied here not from the outside in the form of radiation of shorter wavelength.

A distinction is made between chemiluminescence and bioluminescence. Chemiluminescence refers to a chemical reaction resulting in an excited molecule which luminesces itself when the excited electrons return to the ground state. If this reaction is catalysed by an enzyme, then this process is called bioluminescence. The enzymes involved in the reaction are generally referred to as luciferases.

Classification of the Species *Clytia gregaria*
Cnidaria→Leptomedusae→Campanulariidae→Clytia gregaria The species *Clytia gregaria* belongs to the cnidaria, especially to the medusae. The bioluminescent or fluorescent phenotype has already been described in 1998 (Ward et al., 1998).

Isolation of cDNA

In order to study the fluorescent activity of the species *Clytia gregaria*, specimens were caught in Friday Harbor in Washington State (USA) and stored in liquid nitrogen. The cDNA library was prepared using exclusively the bioluminescent ring of one medusa specimen. The *Clytia gregaria* cDNA libraries were generated by isolating the RNA by means of isothiocyanate according to the method of Krieg (Krieg et al., 1996).

The cDNA was prepared by carrying out an RT-PCR. To this end, 10 μg of RNA were incubated with reverse transcriptase (Superscribt Gold II) according to the following plan:

| PCR | 1. | 30 seconds | 95° C. |
|-----|----|-----------|--------|
|     | 2. | 6 minutes | 68° C. |
|     | 3. | 10 seconds | 95° C. |
|     | 4. | 6 minutes | 68° C. |
| 17 cycles of step 4 after step 3 | | | |

In order to inactivate the polymerase, the reaction products were incubated at 37° C. with proteinase K for 30 minutes and cDNA was precipitated with ethanol. The cDNA was dissolved in water and incubated with SfiI at 37° C. for one hour. The reaction products were gel-filtrated in order to remove small fragments. The fractionated cDNA was then ligated into the SfiI-cut and dephosphorylated λTriplEx2 vector. A λ-phage expression library was then prepared by packing the cloned cDNA fragments into λ phages by means of the in vitro packing system SMART cDNA Library Construction Kits (Clontech).

The recombinant phages containing a cDNA insertion with potential expression of fluorescent proteins were identified by carrying out a "library screening".

To this end, bacterial lawns of transformed *E. coli* XL1-Blue were plated on 90 mm culture dishes and incubated at 31° C. for 12-15 hours. Induction of protein expression was started by adding to the plates 60 μl of a 20 mM IPTG (isopropylthiogalactoside) solution. After 24 hours of incubation at room temperature, the plates were stored at 4° C. for 72 hours. This was followed by measuring the fluorescence.

To this end, the bacteria were irradiated using an argon laser (LGN502) with 100 mV at 488 nm or 366 nm (UVL21). The fluorescence was measured using a 510 nm ZSV filter.

To isolate the clones and for spectral analysis, the biomass of fluorescence-positive clones was removed from the culture plates and resuspended in PBS (phosphate buffered saline). The cells were disrupted by means of ultrasound. After clarifying the lysate by centrifugation, the fluorescence of the supernatant was determined in a fluorimeter.

A fluorescent protein was identified. The fluorescent protein was referred to as CGFP (fluorescence protein of *clytia gregaria*). The fluorescent protein CGFP is illustrated in detail below.

CGFP

The fluorescent protein CGFP shows the highest homology at the amino acid level to Aequoria GFP with an identity of 44% (depicted in Example 8; FIG. 5). At the nucleic acid level, the identity is below 30% (depicted in Example 9; FIG. 6). The BLAST method was used for sequence comparison (Altschul et al., 1997).

The invention also relates to functional equivalents of CGFP. Functional equivalents are those proteins which have comparable physicochemical properties and which are at least 70% homologous. Preference is given to a homology of 80% or 90%. Particular preference is given to a homology of 95%.

The fluorescent protein CGFP is suitable as a reporter gene for cellular systems, especially for receptors, for ion channels, for transporters, for transcription factors or for inducible systems.

The fluorescent protein CGFP is suitable as a reporter gene in bacterial and eukaryotic systems, especially in mammalian cells, in bacteria, in yeasts, in baculo, in plants.

The fluorescent protein CGFP is suitable as a reporter gene for cellular systems in combination with bioluminescent or chemiluminescent systems, especially systems with luciferases, with oxygenases, with phosphatases.

The fluorescent protein CGFP is suitable as a marker protein, especially in FACS (fluorescence activated cell sorter) sorting.

The fluorescient protein CGFP is suitable as a fusion protein, especially for receptors, for ion channels, for transporters, for transcription factors, for proteinases, for kinases, for phosphodiesterases, for hydrolases, for peptidases, for transferases, for membrane proteins, for glycoproteins.

The fluorescent protein CGFP is suitable for immobilization, especially by antibodies, by biotin, by magnetic or magnetizable carriers.

The fluorescent protein CGFP is suitable as a protein for energy transfer systems, especially the FRET (Fluorescence Resonance Energy Transfer), BRET (Bioluminescence Resonance Energy Transfer), FET (field effect transistors), FP (fluorescence polarization), HTRF (Homogeneous time-resolved fluorescence) systems.

The fluorescent protein CGFP is suitable as a label of substrates or ligands, especially for proteases, for kinases, for transferases.

The fluorescent protein CGFP is suitable for expression in bacterial systems, especially for titer determination, as substrates for biochemical systems, especially for proteinases and kinases.

The fluorescent protein CGFP is suitable as a marker, especially coupled to antibodies, coupled to enzymes, coupled to receptors, coupled to ion channels and other proteins.

The fluorescent protein CGFP is suitable as a reporter gene in pharmacological drug screening, especially in HTS (High Throughput Screening).

The fluorescent protein CGFP is suitable as a component of detection systems, especially for ELISA (enzyme-linked immunosorbent assay), for immunohistochemistry, for Western blotting, for confocal microscopy.

The fluorescent protein CGFP is suitable as a marker for the analysis of interactions, especially for protein-protein interactions, for DNA-protein interactions, for DNA-RNA interactions, for RNA-RNA interactions, for RNA-protein interactions (DNA deoxyribonucleic acid; RNA: ribonucleic acid).

The fluorescent protein CGFP is suitable as a marker or fusion protein for expression in transgenic organisms, especially in mice, in rats, in hamsters and other mammals, in primates, in fish, in worms, in plants.

The fluorescent protein CGFP is suitable as a marker or fusion protein for analysing embryonic development.

The fluorescent protein CGFP is suitable as a marker via a coupling mediator, especially via biotin, via NHS(N-hydroxysulphosuccimides), via CN-Br.

The fluorescent protein CGFP is suitable as a reporter coupled to nucleic acids, especially to DNA, to RNA.

The fluorescent protein CGFP is suitable as a reporter coupled to proteins or peptides.

The fluorescent protein CGFP coupled to nucleic acids or peptides is suitable as a probe, especially for Northern blots, for Southern blots, for Western blots, for ELISA, for nucleic acid sequencings, for protein analyses, chip analyses.

The fluorescent protein CGFP is suitable as a label of pharmacological formulations, especially of infectious agents, of antibodies, of small molecules.

The fluorescent protein CGFP is suitable for geological studies, especially for sea currents, groundwater currents and river currents.

The fluorescent protein CGFP is suitable for expression in expression systems, especially in in-vitro translation systems, in bacterial systems, in yeast systems, in baculo systems, in viral systems, in eukaryotic systems.

The fluorescent protein CGFP is suitable for visualizing tissues or cells in surgical procedures, especially in invasive, in noninvasive, in minimally invasive procedures.

The fluorescent protein CGFP is also suitable for labeling tumour tissues and other phenotypically altered tissues, especially in histological examination, in surgical interventions.

The invention also relates to purifying the fluorescent protein CGFP, especially as wild-type protein, as fusion protein, as mutagenized protein.

The invention also relates to the use of the fluorescent protein CGFP in the field of cosmetics, especially of bath additives, of lotions, of soaps, of body paints, of toothpaste, of body powders.

The invention also relates to the use of the fluorescent protein CGFP for colouring, especially of food, of bath additives, of ink, of textiles, of plastics.

The invention also relates to the use of the fluorescent protein CGFP for the colouring of paper, especially of greeting cards, of paper products, of wallpapers, of handicraft articles.

The invention also relates to the use of the fluorescent protein CGFP for the colouring of liquids, especially for water pistols, for fountains, for beverages, for ice cream.

The invention also relates to the use of the fluorescent protein CGFP for producing toys, especially finger paints, face paints.

The invention relates furthermore to nucleic acid molecules, selected from the group consisting of
a) nucleic acid molecules encoding the polypeptide disclosed by SEQ ID NO: 2;
b) nucleic acid molecules containing the sequence depicted by SEQ ID NO: 1;
c) nucleic acid molecules whose complementary strand hybridizes under stringent conditions with a nucleic acid molecule of a) or b) and which have the biological function of a fluorescent protein;
d) nucleic acid molecules which differ from those mentioned under c) due to the degeneracy of the genetic code;
e) nucleic acid molecules whose sequences are at least 95% homologous to SEQ ID NO: 1 and which have the biological function of a fluorescent protein; and
f) nucleic acid molecules whose sequences are at least 65% homologous to SEQ ID NO: 1 and which have the biological function of a fluorescent protein.

The invention relates to the abovementioned nucleic acid molecules whose sequence contains a functional promoter 5' of the sequence.

The invention also relates to nucleic acid molecules as described above which are a part of recombinant DNA or RNA vectors.

The invention relates to organisms which contain such a vector.

The invention refers to oligonucleotides, having more than 10 contiguous nucleotides which are identical or complementary to the DNA or RNA sequence of the CGFP molecules.

The invention relates to fluorescent proteins which are encoded by the above-described nucleotide sequences.

The invention refers to methods of expressing the fluorescent polypeptides according to the invention in bacteria, eukaryotic cells or in in vitro expression systems.

The invention also relates to methods of purifying/isolating a fluorescent polypeptide according to the invention.

The invention relates to peptides, having more than 5 contiguous amino acids which are recognized immunologically by antibodies to the fluorescent proteins according to the invention.

The invention relates to the use of the fluorescent proteins according to the invention as marker genes and reporter genes, in particular for pharmacological drug screening and diagnostics.

Expression of the Fluorescent Proteins According to the Invention

Expression refers to the production of a molecule which, after introduction of the gene into a suitable host cell, allows the foreign gene cloned into an expression vector to be transcribed and translated. Expression vectors contain the control signals required for expression of genes in cells of prokaryotes or eukaryotes.

Expression vectors may be constructed in principle in two different ways. In the case of "transcription fusions", the protein encoded by the cloned-in foreign gene is synthesized as an authentic, biologically active protein. To this end, the expression vector carries all 5' and 3' control signals required for expression.

In the case of "translation fusions", the protein encoded by the cloned-in foreign gene is expressed as a hybrid protein together with another protein which can be readily detected. The 5' and 3' control signals required for expression, including the start codon and possibly part of the sequences coding for the N-terminal regions of the hybrid protein to be formed, are derived from the vector. The additional protein part introduced not only stabilizes, in many cases, the protein encoded by the cloned-in foreign gene against degradation by cellular proteases but can also be used for detecting and isolating the hybrid protein formed. Expression may be either transient or stable. Suitable host organisms are bacteria, yeasts, viruses and eukaryotic systems.

Purification of the Fluorescent Proteins According to the Invention

The isolation of proteins (also after overexpression) is frequently referred to as protein purification. A multiplicity of established methods and processes are available for protein purification.

Solid-liquid separation is a basic operation in protein isolation procedures. This process step is required both in the removal of cells from the culture medium and in clarifying the crude extract, after cell disruption and removal of the cell debris, in removing precipitates after precipitations, etc. It is carried out by way of centrifugation and filtration.

By obtaining intracellular proteins requires the cell wall to be destroyed or made permeable. Depending on the scale and organism, high-pressure homogenizers or stirred ball mills or glass bead mills are used for this purpose. On the laboratory scale, mechanical cell integration and ultrasound treatment are used inter alia.

Various precipitation methods involving salts (in particular ammonium sulphate) or organic solvents (alcohols, acetone) are a rapid and deficient method of concentrating proteins, both for extracellular and intracellular proteins (after cell disruption). When purifying intracellular proteins, removal of the soluble nucleic acids is desirable (precipitation with streptomycin or protamine sulphate, for example). The recovery of extracellular proteins frequently involves the addition of carriers (e.g. starch, kieselguhr), prior to addition of the precipitants, in order to obtain better manageable precipitates.

Numerous chromatographic and partition methods are available for fine purification (absorption chromatography and ion exchange chromatography, gel filtration, affinity chromatography, electrophoreses). Column chromatography is also applied on the industrial scale. Affinity chromatography which makes purification factors of up to several 100 per step possible is especially important on the laboratory scale.

Extracellular proteins are obtained in relatively diluted solutions. Like extracellular proteins, they must be concentrated prior to further use. Ultrafiltration is a proven method, also on the industrial scale, in addition to the methods already mentioned.

Inorganic salts are frequently undesired accompanying substances of proteins in specific applications. They may be removed, inter alia, by gel filtration, dialysis and diafiltration.

Numerous proteins are used as dry preparations. Important drying processes are vacuum drying, freeze drying and spray drying.

Nucleotide and Amino Acid Sequences

The fluorescent protein CGFP is encoded by the following nucleotide sequence (SEQ ID NO: 1):

```
5'-
atgactgcacttaccgaaggagcaaaactgttcgagaaagaaattccctacattaca gagttggaaggagacgttgaaggaatgaaattcatcatcaaaggtgaaggtactggc gacgctactactggcaccatcaaagcgaaatatatttgcacaactggtgaccttcct gtaccatgggctaccatcttgagtagtttgtcgtatggtgttttctgtttcgctaag tatccacgccacattgccgacttttcaagagcacacaaccagatggttattcacaa gacagaatcattagttttgacaatgatggacaatacgatgtcaaagccaaggttact tatgaaaacggaacactttataatagagtcacagtcaaaggtactggcttcaaatca aacggcaacatccttggtatgagagttctctaccattcaccaccacacgctgtctac atccttcctgaccgtaaaaatggtggcatgaaaattgaatacaataaggctttcgac gttatgggcggtggtcaccaaatggcgcgtcacgcccaattcaataaaccactagga gcctgggaagaagattatccgttgtatcatcatcttaccgtatggacttctttcgga aaagatccggatgatgatgaaactgaccatttgaccatcgtcgaagtcatcaaagct gttgatttggaaacataccgttga-3'.
```

This results in an amino acid sequence of (SEQ ID NO: 2):

```
MTALTEGAKLFEKEIPYITELEGDVEGMKFIIKGEGTGDATTGTIKAKYICTTGDLP

VPWATILSSLSYGVFCFAKYPRHIADFFKSTQPDGYSQDRIISFDNDGQYDVKAKVT

YENGTLYNRVTVKGTGFKSNGNILGMRVLYHSPPHAVYILPDRKNGGMKIEYNKAFD

VMGGGHQMARHAQFNKPLGAWEEDYPLYHHLTVWTSFGKDPDDDETDHLTIVEVIKA

VDLETYR
```

These sequences can be found in the sequence listing.

DESCRIPTION OF THE FIGURES

FIG. 6 depicts the alignment of CFGP, GFP (*Aquoria*) and GFP (*Renilla*) at the amino acid level.

CGFP_Cly: CGFP from *Clytia gregaria*
GFP_Ren: GFP from *Renilla*
GFP_Aeq. GFP from *Aequoria*

FIGS. 7A-7E depict the alignment of CFGP, GFP (*Aquoria*) and GFP (*Renilla*) at the nucleic acid level.

CGFP_Cly: CGFP from *Clytia gregaria*
GFP_Ren: GFP from *Renilla*
GFP_Aeq. GFP from *Aequoria*

EXAMPLES

Example 1

The vector used for preparing the construct illustrated below was the plasmid pTriplEx2 from Clontech. The derivative of said vector was referred to as pTriplEx2-CGFP. The pTriplEx2-CGFP vector was used for expressing CGFP in bacterial systems.

Figure 1:
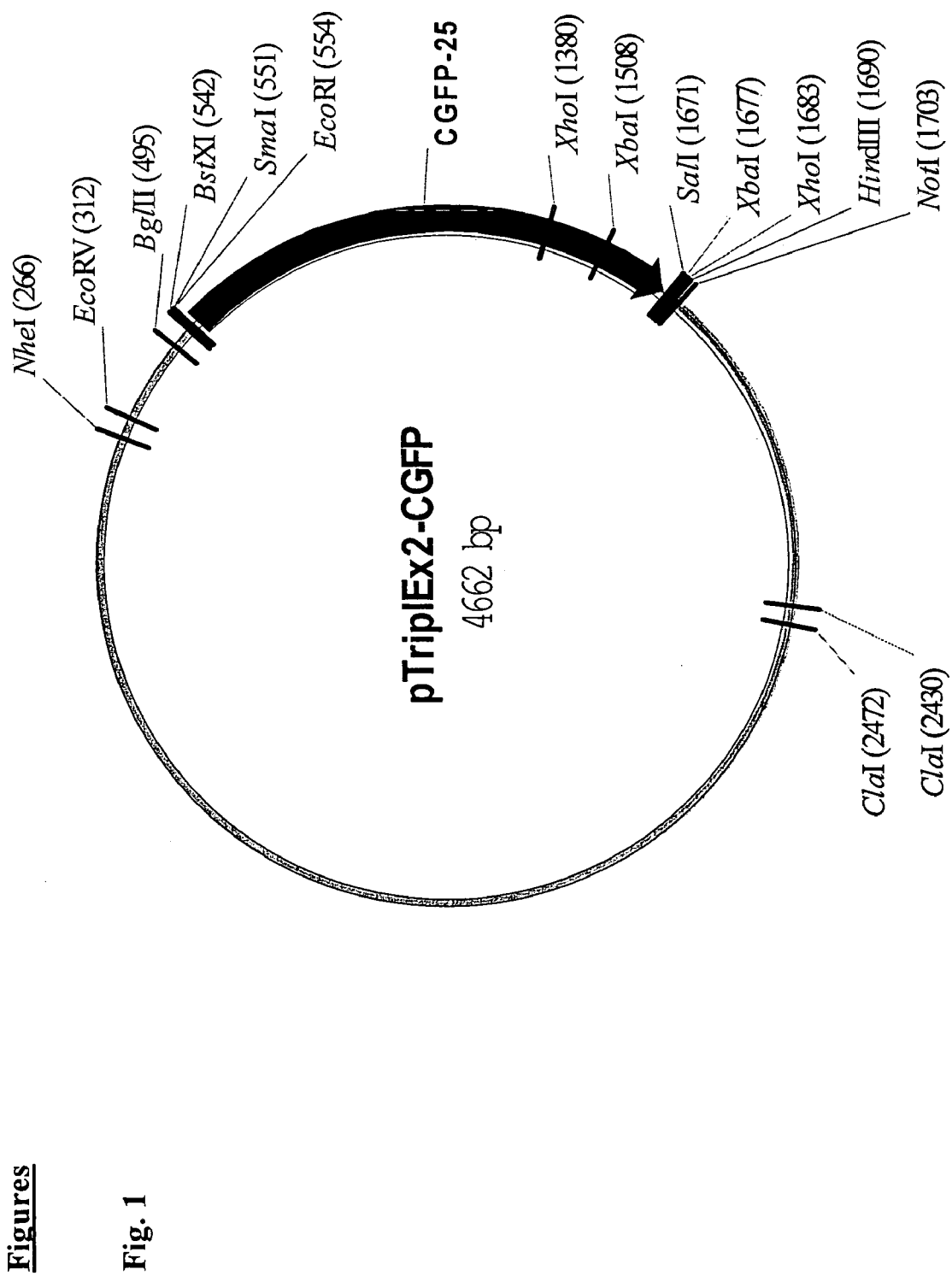
FIG. 1 depicts the plasmid map of the pTriplEX2-CGFP vector.

FIG. 1 depicts the plasmid map of the pTriplEX2-CGFP vector.

Example 2

The vector used for preparing the construct illustrated below was the plasmid pcDNA3.1(+) from Clontech. The derivative of said vector was referred to as pcDNA3-CGFP. The pcDNA3-CGFP vector was used for expressing CGFP in eukaryotic systems.

Figure 2:
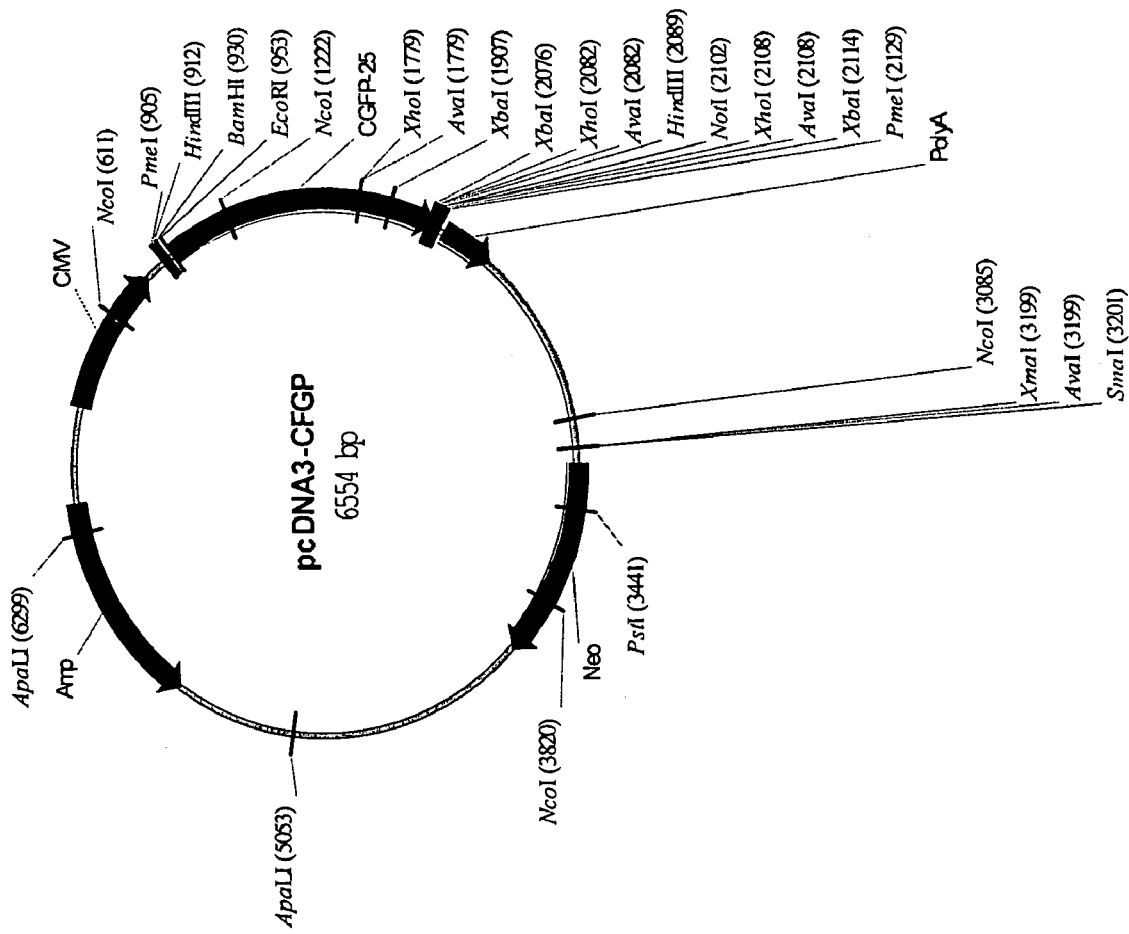
FIG. 2 depicts the plasmid map of the pcDNA3-CGFP vector.

FIG. 2 depicts the plasmid map of the pcDNA3-CGFP vector.

Example 3

Bacterial Expression

Bacterial expression was carried out in the *E. coli* strain BL21(DE3) by transforming the bacteria with the expression plasmids pTriplEX2-CGFP and pTriplEX2. The transformed bacteria were incubated in LB medium at 37° C. for 3 hours and expression was induced for 4 hours by adding IPTG up to a final concentration of 1 mM. The induced bacteria were harvested by centrifugation, resuspended in PBS and sonicated. The fluorescence was determined with the aid of a fluorimeter.

Example 4

Eukaryotic Expression

Constitutive eukaryotic expression was carried out in CHO cells by transfecting said cells with the expression plasmids pcDNA3-CGFP and pcDNA3.1(+) in transient experiments. To this end, 10000 cells per well were plated in DMEM-F12 medium on 96-well microtiter plates and incubated at 37° C. overnight. Transfection was carried out with the aid of the Fugene 6 kit (Roche) according to the manufacturer's information. The transfected cells were incubated in DMEM-F12 medium at 37° C. overnight. The fluorescence was measured in a fluorimeter at room temperature.

Figure 3:
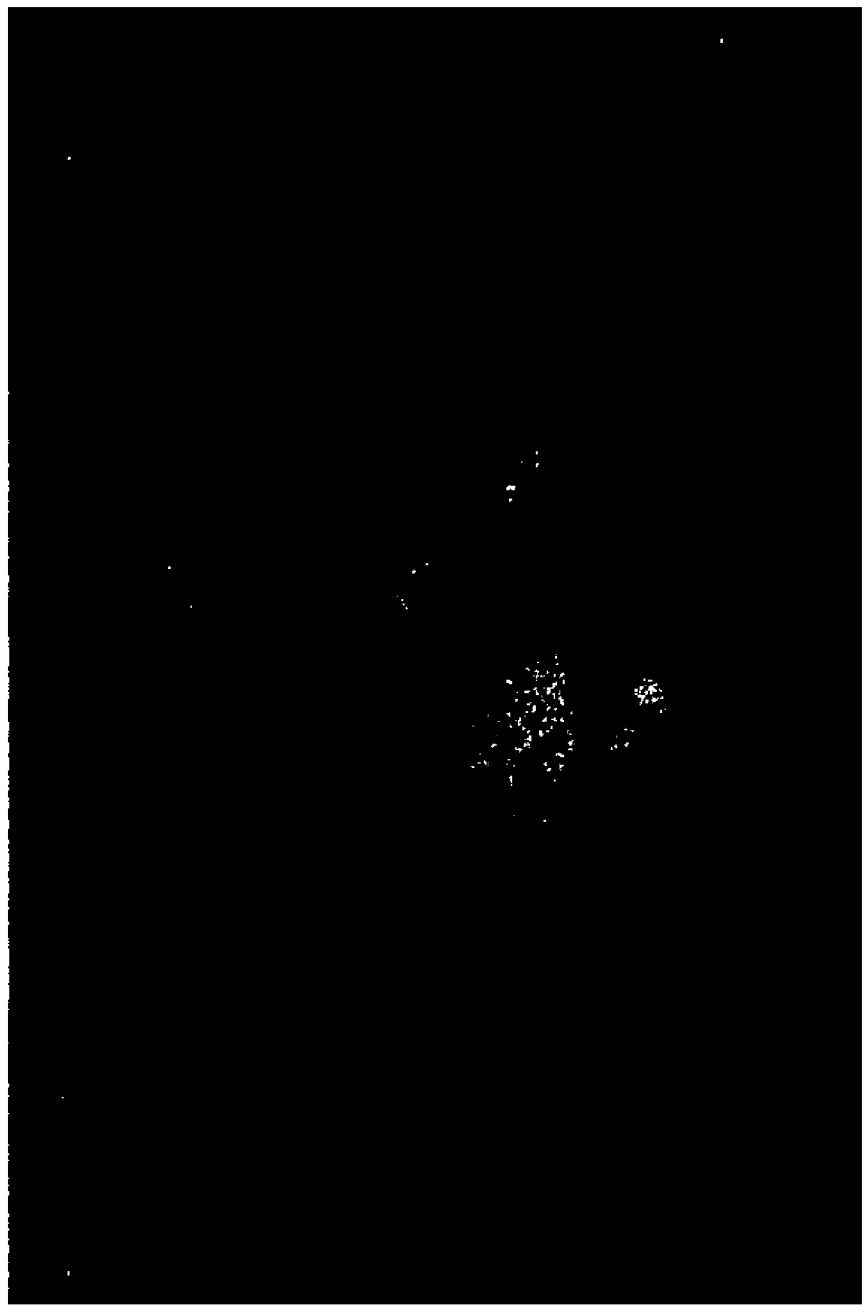
FIG. 3 depicts the transient expression of CGFP in CHO cells in the pcDNA3-CGFP expression vector. The figure depicts the microscopic image of the transiently transfected cells, at an excitation of 480 nm and an emission of 520 nm.

FIG. 3 depicts expression of CGFP in CHO cells.

Example 5

Spectrum of the Fluorescent Protein CGFP

To measure the emission spectrum, *E. coli* BL21(DE3) were transformed with the plasmids pTriplEX2-CGFP and pTriplEX2. Induction was carried out by adding 1 mM IPTG and incubating at 37° C. for 4 hours. The bacteria were subsequently harvested and resuspended in PBS. The lysis was carried out using ultrasound. Subsequently, fluorescence was measured in a fluorimeter.

Figure 4:
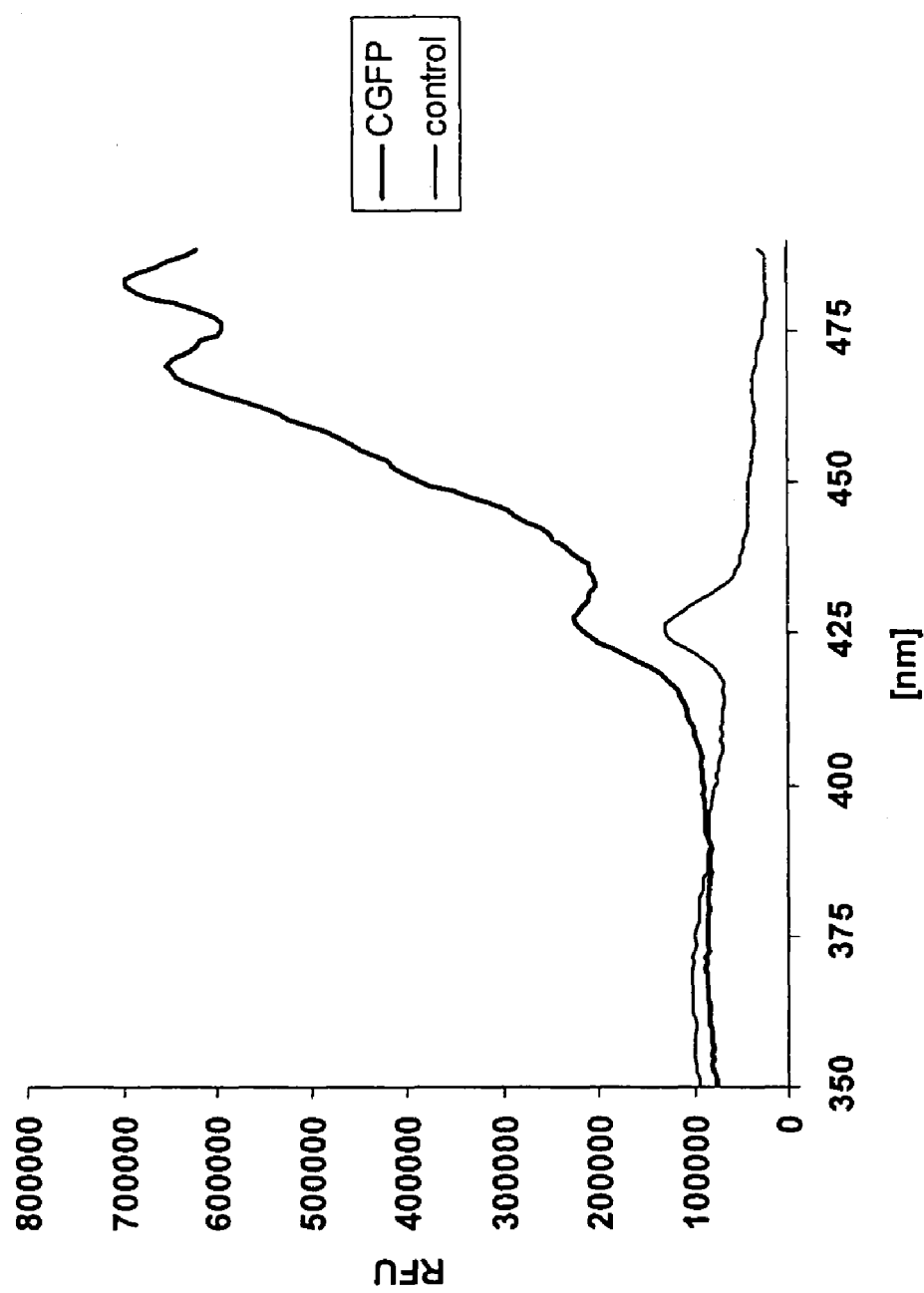
FIG. 4 depicts the excitation of CGFP and of the control lysate.

FIG. 4 depicts the excitation of CGFP and of the control lysate.

Figure 5:
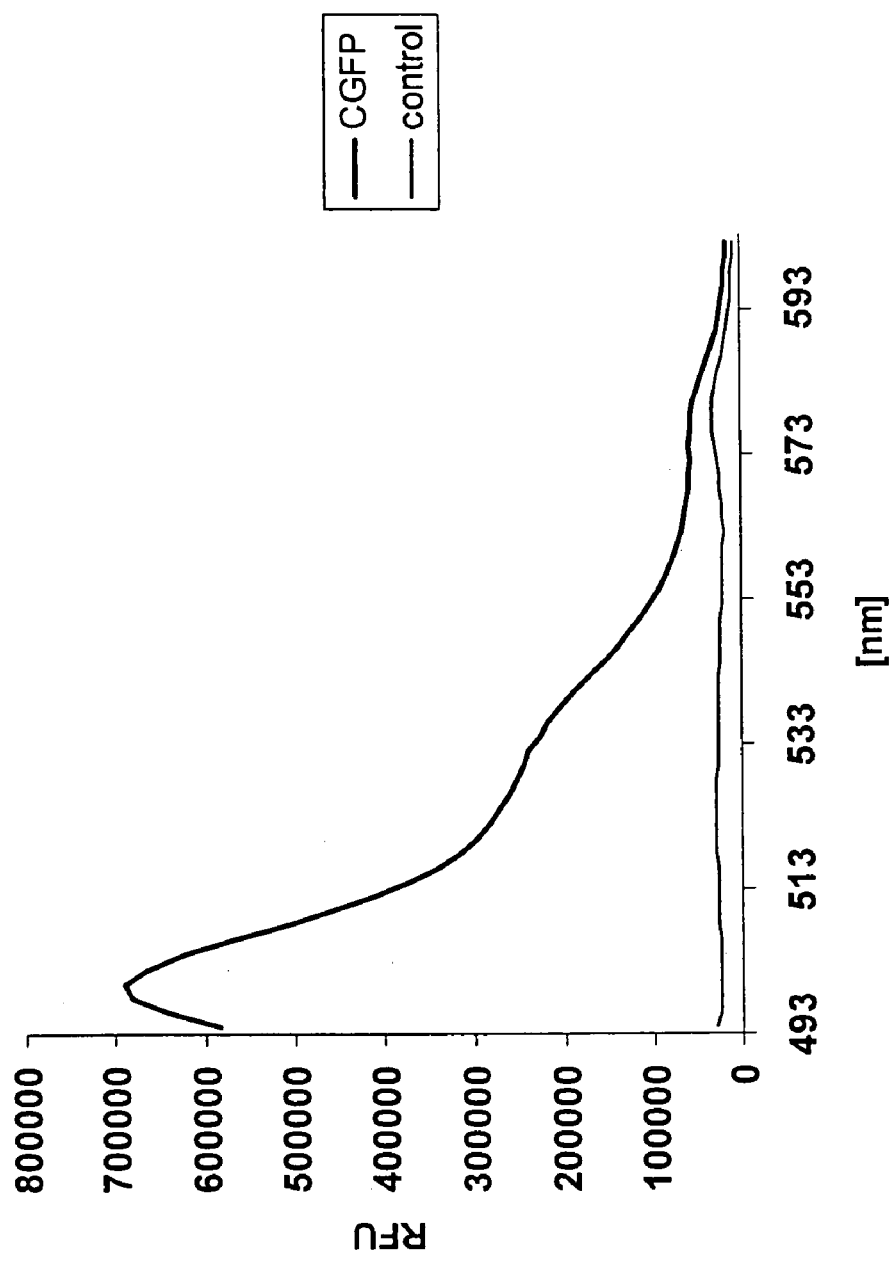
FIG. 5 depicts the emission of CGFP and of the control lysate.

FIG. 5 depicts the emission of CGFP and of the control lysate.

Example 6

BLAST

Result of a BLAST analysis of CFGP at the amino acid level.

>AA2002:ABB06186 Abb06186 Green fluorescent protein GFPxm19 SEQ ID, NO: 15. 5/2002, Length = 271, Score = 219 bits (558), Expect = 3e−56, Identities = 102/228 (44%), Positives = 151/228 (65%), Gaps = 3/228 (1%)
>gb|AAK02065.1| mutant green fluorescent protein [synthetic construct], Length = 238, Score = 219 bits (557), Expect = 4e−56, Identities = 102/227 (44%), Positives = 150/227 (65%), Gaps = 3/227 (1%)
>gb|AAL33915.1|AF435430_1 green fluorescent protein [*Aequorea macrodactyla*], Length = 238, Score = 218 bits (556), Expect = 5e−56, Identities = 102/227 (44%), Positives = 150/227 (65%), Gaps = 3/227 (1%)
>gb|AAL33918.1|AF435433_1 green fluorescent protein [*Aequorea macrodactyla*], Length = 238, Score = 218 bits (555), Expect = 7e−56, Identities = 101/227 (44%), Positives = 149/227 (65%), Gaps = 3/227 (1%)
>gb|AAL33916.1|AF435431_1 green fluorescent protein [*Aequorea macrodactyla*], Length = 238, Score = 218 bits (554), Expect = 9e−56 Identities = 102/227 (44%), Positives = 150/227 (65%), Gaps = 3/227 (1%)
>gb|AAL33917.1|AF435432_1 orange fluorescent protein [*Aequorea macrodactyla*], Length = 238, Score = 218 bits (554), Expect = 9e−56, Identities = 101/227 (44%), Positives = 149/227 (65%), Gaps = 3/227 (1%)
>AA2002:ABB06185 Abb06185 Green fluorescent protein GFPxm18 SEQ ID, NO: 13. 5/2002, Length = 271, Score = 217 bits (552), Expect = 1e−55, Identities = 101/228 (44%), Positives = 151/228 (65%), Gaps = 3/228 (1%)
>AA2002:ABB06184 Abb06184 Green fluorescent protein GFPxm16 SEQ ID, NO: 11. 5/2002, Length = 271, Score = 216 bits (551), Expect = 2e−55, Identities = 101/228 (44%), Positives = 150/228 (65%), Gaps = 3/228 (1%)
>AA2002:ABB06181 Abb06181 Green fluorescent protein GFPxm SEQ ID, NO: 5. 5/2002, Length = 271, Score = 216 bits (551), Expect = 2e−55, Identities = 101/228 (44%), Positives = 150/228 (65%), Gaps = 3/228 (1%)
>gb|AAL33912.1|AF435427_1 green fluorescent protein [*Aequorea macrodactyla*], Length = 238, Score = 216 bits (551), Expect = 2e−55, Identities = 101/227 (44%), Positives = 150/227 (65%), Gaps = 3/227 (1%)
>gb|AAK02064.1| mutant green fluorescent protein [synthetic construct], Length = 238, Score = 216 bits (551), Expect = 2e−55, Identities = 101/227 (44%), Positives = 150/227 (65%), Gaps = 3/227 (1%)

Example 7

BLAST

Result of a BLAST analysis of CFGP at the nucleic acid level.

>gb|AF468563.1| *Crassostrea gigas* clone c077 microsatellite sequence, Length = 415, Score = 41.1 bits (21), Expect = 1.4,
Identities = 25/27 (92%)
>gb|AC079685.2| *Oryza sativa* chromosome 10 clone OSJNBb0012A20, complete sequence, Length = 131599, Score = 41.1 bits (21),
Expect = 1.4, Identities = 27/30 (90%)
>gb|AF427906.1|AF427906 *Solenopsis globularia littoralis* putative odorant binding protein, precursor (Gp-9) gene, complete cds, Length = 1767, Score = 41.1 bits (21), Expect = 1.4, Identities = 23/24 (95%)
>gb|AF297617.1|AF297617 *Echinococcus granulosus* genotype 1 mitochondrion, complete genome, Length = 13588, Score = 41.1 bits (21), Expect = 1.4, Identities = 23/24 (95%).

Example 8

FIG. 6 depicts the alignment of CFGP, GFP (*Aquoria*) and GFP (*Renilla*) at the nucleic acid level.

Example 9

FIGS. 7A-7E depict the alignment of CFGP, GFP (*Aquoria*) and GFP (*Renilla*) at the amino acid level.

Literature/Patents

U.S. Pat. No. 4,777,128
U.S. Pat. No. 4,927,923
U.S. Pat. No. 5,162,508
U.S. Pat. No. 5,279,943
U.S. Pat. No. 5,958,713
U.S. Pat. No. 6,172,188
U.S. Pat. No. 6,232,107
U.S. Pat. No. 6,436,682
WO199623898
WO199711094
WO 199728261
WO1998/02571
WO199949019
WO200071565
WO200134824
WO200168824
WO200257451

Alam J, Cook J L. Reporter genes: application to the study of mammalian gene transcription. *Anal Biochem.* 1990 Aug. 1; 188(2):245-54

Altschul, Stephen F., Thomas L. Madden, Alejandro A. Schäffer, Jinghui Zhang, Zheng Zhang, Webb Miller, and David J. Lipman (1997); Gapped BLAST and PSI-BLAST: a new generation of protein database search programs; *Nucleic Acids Res.* 25:3389-3402

Cardullo et al. (1988) Detection of nucleic acid hybridization by nonradiative fluorescence resonance energy transfer; *Proc. Natl. Acad. Sci. U.S.A.* 85:8790-8794

Cormier, M. J., Hori, K., Karkhanis, Y. D., Anderson, J. M., Wampler, J. E., Morin, J. G., and Hastings, J. W. (1973) Evidence for similar biochemical requirements for bioluminescence among the coelenterates. *J. Cell. Physiol.* 81, 291-298.

Cormier, M. J., Hori, K., and Anderson, J. M. (1974) Bioluminescence in coelenterates. *Biochim. Biophys. Acta* 346, 137-164.

Cullen Bryan R., Malim Michael H., Secreted placental alkaline phosphatase as a eukaryotic reporter gene. *Methods in Enzymology.* 216:362ff Davenport, D. and Nicol, J. A. C. (1955) Luminescence in Hydromedusae. *Proc. R. Soc. B* 144, 399-411.

Delagrave et al., Red-shifted excitation mutants of the green fluorescent protein, Bio/Technology 13(2):151-154 (1995)

Ehrig et al., Green-fluorescent protein mutants with altered fluorence excitationspectra, FEBS Letters 367:163-166 (1995)

Hastings, J. W. and Morin, J. G. (1969) Comparative biochemistry of calcium-activated photoproteins from the ctenophore, *Mnemiopsis* and the coelenterates *Aequorea, Obelia*, and *Pelagia. Biol. Bull.* 137, 402.

Heim et al., (1996) Engineering green fluorescent protein for improved brightness, longer wavelengths and fluorescence resonance energy transfer, Current Biology 6(2):178-182 (1996).

Inouye S, Tsuji F I. (1994) *Aequorea* green fluorescent protein. Expression of the gene and fluorescence characteristics of the recombinant protein. *FEBS Lett* 1994 Mar. 21; 341(2-3):277-80

Johnson, F. H., Shimomura, O., Saiga, Y., Gershman, L. C., Reynolds, G. T., and Waters, J. R. (1962) Quantum efficiency of *Cypridina* luminescence, with a note on that of *Aequorea. J. Cell. Comp. Physiol.* 60, 85-103.

Krieg, S., Castles, C., Allred, D., Benedix, M., Fuqua S., RNA from air-dried frozen sections for RT-PCR and differential display. *Biotechniques.* 1996 September; 21(3):425-8.

Levine, L. D. and Ward, W. W. (1982) Isolation and characterization of a photoprotein, "phialidin", and a spectrally unique green-fluorescent protein from the bioluminescent jellyfish *Phialidium gregarium. Comp. Biochem. Physiol.* 72B, 77-85.

Mitra et al., Fluorescence resonance energy tranfer between blue-emitting and red-shifted excitation derivatives of the green fluorescent protein, Gene 73(1):13-17 (1996).

Morin, J. G. and Hastings, J. W. (1971) Biochemistry of the bioluminescence of colonial hydroids and other coelenterates. *J. Cell. Physiol.* 77, 305-311.

Morin, J. G. and Hastings, J. W. (1971) Energy transfer in bioluminescent system. *J. Cell. Physiol.* 77, 313-318.

Phillips G N. Structure and dynamics of green fluorescent protein. *Curr Opin Struct Biol.* 1997 December; 7(6):821-7

Shimomura O., Bioluminescence in the sea: photoprotein systems. *Symp Soc Exp Biol.* 1985; 39:351-72.

Snowdowne K W, Borle A B. Measurement of cytosolic free calcium in mammalian cells with aequorin. *Am J Physiol.* 1984 November; 247(5 Pt 1):C396-408.

Ward, W. W. (1998) Biochemical and physical properties of green fluorescent protein. In: *Green Fluorescent Protein: Properties, Applications, and Protocols* (Chalfie, M. and Kain, S., eds) pp. 45-70. Wiley-Liss, Inc.

Ward et al., Energy Transfer Via Protein-Protein Interation in *Renilla* Bioluminescence Photochemistry and Photobiology 27:389-396 (1978).

Wampler, J. E., Hori, K., Lee, J. W., and Cormier, M. J. (1971) Structured bioluminescence. Two emitters during both the in vitro and the in vivo bioluminescence of the sea pansy, *Renilla* Biochemistry 10, 2903-2909.

Wampler, J. E., Karkhanis, Y. D., Morin, J. G., Cormier, M. J. (1973) Similarities in the bioluminescence from the *Pennatulacea. Biochim. Biophys. Acta* 314, 104-109.

Yang Te-Tuan, Sinai Parisa, Kitts Paul A. Kain Seven R., Quantification of gene expresssion with a secreted alkaline phosphatase reporter system. *Biotechnique.* 1997 23(6)1110ff

The invention claimed is:

1. An isolated nucleic acid molecule, selected from the group consisting of:
   a) a nucleic acid molecule encoding a polypeptide having the amino acid sequence of SEQ ID NO: 2;
   b) a nucleic acid molecule comprising the sequence of SEQ ID NO: 1;
   c) a nucleic acid molecule which is at least 95% homologous to the full-length nucleic acid sequence SEQ ID NO: 1 and whose complementary strand hybridizes under stringent conditions with a nucleic acid molecule encoding the amino acid sequence of SEQ ID NO: 2 or with a nucleic acid molecule consisting of the nucleic acid sequence of SEQ ID NO: 1, and which encodes a fluorescent protein.

2. The isolated nucleic acid molecule according to claim 1, wherein said nucleic acid molecule further comprises a functional promoter operably linked to its 5' end.

3. A recombinant vector comprising the isolated nucleic acid molecule of claim 1 or claim 2.

4. A host cell, which contains the vector according to claim 3.

5. A method of determining whether a gene of interest, or fragment thereof, has been expressed comprising monitoring the fluorescence of a polypeptide encoded by a fusion gene and comparing it to the fluorescence when the gene or fragment is not expressed, wherein said fusion gene comprises the nucleic acid of claim 1 operably linked to said gene of interest, or fragment thereof.

6. The recombinant vector of claim 3, wherein the vector is an expression vector.

7. The vector of claim 6, wherein said vector comprises an inducible promoter.

8. A method of producing a fluorescent protein encoded by the nucleic acid of claim 1 in a host cell, wherein said host cell is a bacteria cell or a eukaryotic cell comprising the steps of:
   (i) transforming said host cell with the expression vector of claim 6, and
   (ii) growing said host cell from step (i) under conditions that permit said fluorescent polypeptide to be produced in the transformed host cell of part (i).

9. An isolated nucleic acid molecule, selected from the group consisting of:
   a) a nucleic acid molecule encoding a polypeptide having the amino acid sequence of SEQ ID NO: 2;
   b) a nucleic acid molecule comprising the sequence of SEQ ID NO: 1;
   c) a nucleic acid molecule which is at least 95% homologous to the full-length nucleic acid sequence SEQ ID NO:1 and whose complementary strand hybridizes under stringent conditions with a nucleic acid molecule encoding the amino acid sequence of SEQ ID NO: 2 or with a nucleic acid molecule consisting of the nucleic acid sequence of SEQ ID NO: 1, and which encodes a fluorescent protein having an excitation peak of about 475 nm and an emission peak of about 493 nm.

10. The method of claim 8, further comprising isolating the fluorescent polypeptide.

* * * * *

SEQUENCE LISTING

<160> NUMBER OF SEQ ID NOS: 2

<210> SEQ ID NO 1
<211> LENGTH: 708
<212> TYPE: DNA
<213> ORGANISM: Clytia gregaria

<400> SEQUENCE: 1

```
atgactgcac ttaccgaagg agcaaaactg ttcgagaaag aaattcccta cattacagag      60
ttggaaggag acgttgaagg aatgaaattc atcatcaaag gtgaaggtac tggcgacgct     120
actactggca ccatcaaagc gaaatatatt tgcacaactg gtgaccttcc tgtaccatgg     180
gctaccatct tgagtagttt gtcgtatggt gttttctgtt tcgctaagta tccacgccac     240
attgccgact ttttcaagag cacacaacca gatggttatt cacaagacag aatcattagt     300
tttgacaatg atggacaata cgatgtcaaa gccaaggtta cttatgaaaa cggaacactt     360
tataatagag tcacagtcaa aggtactggc ttcaaatcaa acggcaacat ccttggtatg     420
agagttctct accattcacc accacacgct gtctacatcc ttcctgaccg taaaaatggt     480
ggcatgaaaa ttgaatacaa taaggctttc gacgttatgg gcggtggtca ccaaatggcg     540
cgtcacgccc aattcaataa accactagga gcctgggaag aagattatcc gttgtatcat     600
catcttaccg tatggacttc tttcggaaaa gatccggatg atgatgaaac tgaccatttg     660
accatcgtcg aagtcatcaa agctgttgat ttggaaacat accgttga                  708
```

<210> SEQ ID NO 2
<211> LENGTH: 235
<212> TYPE: PRT
<213> ORGANISM: Clytia gregaria

<400> SEQUENCE: 2

```
Met Thr Ala Leu Thr Glu Gly Ala Lys Leu Phe Glu Lys Glu Ile Pro
1               5                   10                  15

Tyr Ile Thr Glu Leu Glu Gly Asp Val Glu Gly Met Lys Phe Ile Ile
            20                  25                  30

Lys Gly Glu Gly Thr Gly Asp Ala Thr Thr Gly Thr Ile Lys Ala Lys
        35                  40                  45

Tyr Ile Cys Thr Thr Gly Asp Leu Pro Val Pro Trp Ala Thr Ile Leu
    50                  55                  60

Ser Ser Leu Ser Tyr Gly Val Phe Cys Phe Ala Lys Tyr Pro Arg His
65                  70                  75                  80

Ile Ala Asp Phe Phe Lys Ser Thr Gln Pro Asp Gly Tyr Ser Gln Asp
                85                  90                  95

Arg Ile Ile Ser Phe Asp Asn Asp Gly Gln Tyr Asp Val Lys Ala Lys
            100                 105                 110

Val Thr Tyr Glu Asn Gly Thr Leu Tyr Asn Arg Val Thr Val Lys Gly
        115                 120                 125

Thr Gly Phe Lys Ser Asn Gly Asn Ile Leu Gly Met Arg Val Leu Tyr
    130                 135                 140

His Ser Pro Pro His Ala Val Tyr Ile Leu Pro Asp Arg Lys Asn Gly
145                 150                 155                 160

Gly Met Lys Ile Glu Tyr Asn Lys Ala Phe Asp Val Met Gly Gly Gly
                165                 170                 175

His Gln Met Ala Arg His Ala Gln Phe Asn Lys Pro Leu Gly Ala Trp
            180                 185                 190
```

```
Glu Glu Asp Tyr Pro Leu Tyr His His Leu Thr Val Trp Thr Ser Phe
        195                 200                 205

Gly Lys Asp Pro Asp Asp Glu Thr Asp His Leu Thr Ile Val Glu
    210             215                 220

Val Ile Lys Ala Val Asp Leu Glu Thr Tyr Arg
225             230                 235
```